(12) United States Patent
Genosar (10) Patent No.: US 7,524,304 B2
(45) Date of Patent: Apr. 28, 2009

(54) DRUG INFUSION DEVICE

(75) Inventor: Amir Genosar, Lafayette, CO (US)

(73) Assignee: SteadyMed, Ltd., Ramat-Gan (IL)

( * ) Notice: Subject to any disclaimer, the term of this patent is extended or adjusted under 35 U.S.C. 154(b) by 292 days.

(21) Appl. No.: 10/544,167

(22) PCT Filed: Feb. 2, 2004

(86) PCT No.: PCT/IL2004/000099

§ 371 (c)(1),
(2), (4) Date: Jul. 29, 2005

(87) PCT Pub. No.: WO2004/067066

PCT Pub. Date: Aug. 12, 2004

(65) Prior Publication Data

US 2006/0079862 A1 Apr. 13, 2006

(30) Foreign Application Priority Data

Feb. 2, 2003 (IL) .................................. 154243

(51) Int. Cl.
*A61M 5/20* (2006.01)
(52) U.S. Cl. .................... 604/135; 604/890.1
(58) Field of Classification Search ............... 604/135, 604/214, 890.1, 31, 65, 67, 131, 232
See application file for complete search history.

(56) References Cited

U.S. PATENT DOCUMENTS

| | | | |
|---|---|---|---|
| 4,652,751 A | 3/1987 | Rundt et al. | |
| 4,678,408 A | 7/1987 | Nason et al. | |
| 5,062,834 A | 11/1991 | Gross et al. | |
| 5,242,406 A | 9/1993 | Zucker et al. | |
| 5,242,565 A * | 9/1993 | Winsel | 204/265 |
| 5,290,240 A * | 3/1994 | Horres, Jr. | 604/131 |
| 5,318,577 A | 6/1994 | Li | |
| 5,354,264 A * | 10/1994 | Bae et al. | 604/21 |
| 5,527,288 A | 6/1996 | Gross et al. | |
| 5,599,438 A | 2/1997 | Shiramizu et al. | |
| 5,743,879 A | 4/1998 | Kriesel | |
| 5,814,020 A | 9/1998 | Gross | |
| 5,820,622 A | 10/1998 | Gross et al. | |
| 5,858,001 A * | 1/1999 | Tsals et al. | 604/135 |
| 5,891,097 A | 4/1999 | Fujita et al. | |
| 6,186,982 B1 * | 2/2001 | Gross et al. | 604/132 |
| 6,413,238 B1 | 7/2002 | Maget | |

(Continued)

FOREIGN PATENT DOCUMENTS

DE 19713082 10/1998

*Primary Examiner*—Nicholas D Lucchesi
*Assistant Examiner*—Victoria P Campbell
(74) *Attorney, Agent, or Firm*—Andrus, Sceales, Starke & Sawall, LLP (57) ABSTRACT

The invention provides a drug delivery infusion device comprising an injection means (18) in fluid connection with a drug reservoir chamber (12) and pressure-generation means (10) coupled to both the drug reservoir (12) and to a liquid-filled control chamber (13), wherein the coupling is such that the liquid-filled control chamber (13) serves to constrain the motion of the pressure-generation means (10), thereby controlling the drug infusion rate, wherein the liquid-filled control chamber (13) is associated with means for controlled depletion of the liquid therein whereby depletion of the volume of liquid in the control chamber enables the pressure-generation means to drive the drug in the reservoir chamber therefrom for infusion thereof.

26 Claims, 5 Drawing Sheets

U.S. PATENT DOCUMENTS

2001/0056259 A1   12/2001   Lamborne et al.
2002/0156464 A1   10/2002   Hooper et al.
2002/0173769 A1 * 11/2002   Gray et al. .................. 604/506

* cited by examiner

DRUG INFUSION DEVICE

CROSS REFERENCE TO RELATED APPLICATIONS

This application is the U.S. national stage application of International Application PCT/IL2004/000099, filed Feb. 2, 2004, which was published on Aug. 12, 2004, as International Publication WO2004/067066 in the English language. The International Application claims priority of Israel Patent Application 154,243, filed Feb. 2, 2003.

CROSS-REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

INCORPORATION-BY-REFERENCE OF MATERIAL SUBMITTED ON A COMPACT DISC

Not applicable.

BACKGROUND OF THE INVENTION (1) Field of the Invention

This invention relates to a system for the administration of drugs and/or biologically active materials by infusion. More particularly, this invention relates to a delivery device in which the gradual reduction of a liquid volume in a control chamber serves as a slow braking device, thus limiting the infusion rate of the drugs or other materials being infused. The reduction of liquid volume may be achieved by chemical or electrical conversion of part of said liquid to a gas which is released to the environment. A pressure-application means such as a spring drives the infusion of the drugs and/or biologically active materials at a controllable and stable rate in accordance with the steady reduction of liquid volume. Where the conversion of liquid to gas is due to electrolysis, the rate of the electrolysis process (for example the production of hydrogen and oxygen from water) is controlled by an electric current. This current is supplied by a battery and can be activated and controlled by an electronic timer or a biomedical control system which reacts to stimuli related to bodily functions, such as temperature, pH, a glucose sensor, muscle contractions, electroencephalography, or electrocardiography, and/or a combination of the above.

(2) Description of Related Art

There have been many approaches to meet the problems of regulating the delivery of drugs and/or biologically active materials (hereinafter collectively referred to as "drugs") in the place and at the proper dose to achieve the desired regulatory effect. Some of these systems depend on the utilization of physical or chemical stimuli which are a result of changes in the biological systems. Such stimuli may include externally measured bodily functions such as temperature, muscle contractions, electroencephalography, electrocardiography; chemical or biological sensors monitoring liquid excretions from the skin, or invasive or minimally invasive sensors to measure various analytes within the body. U.S. Pat. No. 5,820,622, hereby incorporated by reference, describes an exemplary approach to controlling the flow-rate of a drug-delivery device based on input from a sensor needle inserted into the subject's body. The sensor needle uses an enzymatic detector to detect an analyte such as glucose in the subject's plasma, and thereby determine the desired flow-rate of the drug.

The primary delivery methods for drug infusion are infusion pumps utilizing gravity flow and other electrically driven mechanical pumps (peristaltic or syringe pumps) attached to syringes or intravenous tubing which infuse the drugs into the body. In addition, elastomeric balloons can also be utilized as the contraction force. However, all these systems require large, complicated supports along with electronic or mechanical pumps which restrict their portability for ambulatory patients in hospitals or at home.

For ambulatory use there are two main approaches: (1) An electric motor or solenoid drive apparatus connected to a lead screw mechanism which compresses a piston to drive the infusion, and (2) A gas-driven method where the gas generated drives the infusion, generally via a movable membrane or piston-driven pumping chamber. The former approach is extensively described in the prior art, for example in U.S. Pat. No. 4,562,751 and U.S. Pat. No. 4,678,408 and is exemplified by the "MicroMed" product from Medtronic Minimed Inc. (Northridge, Calif.). In these devices, torque is translated to drug pressure and, as a result, the mechanism is very sensitive to friction and thus demands very tight manufacturing tolerances. Moreover, whereas the lead screw method is very accurate and reliable, it is too expensive to be used as a disposable product. Accordingly, the products of this nature suffer from the disadvantage that they require filling "in the field" and the manufacturers are required to provide a maintenance infrastructure. Given the medical importance of the devices, this maintenance becomes a critical issue. Accordingly, much effort has been devoted to the development of inexpensive, disposable ambulatory infusion devices, as described below. The advantage of such a device would be that it would come pre-filled with the drug and, if for whatever reason it malfunctioned, the patient could simply replace it with a further unit.

The prior art describes a number of such disposable devices, which typically employ a gas-driven infusion principle. U.S. Pat. No. 5,318,557 and U.S. Pat. No. 5,527,288 describe an inexpensive, gas-driven infusion device which can be manufactured sufficiently inexpensively in order to constitute a disposable product. The embodiments described therein employ an electrolytic cell for gas production as per U.S. Pat. No. 5,062,834. A similar gas-driven device is described in U.S. Pat. No. 5,354,264. This device utilizes gas pressure from free oxygen and hydrogen derived from the electrolysis of water at the electrodes in negatively charged polymeric hydrogels. Said device ensures that the gas generated remains within the walls of the gas chamber by making said walls "rigid and impermeable to gases". In all these devices, the gas pressure forces the infusion of the drugs through appropriate means into the body, with the pressure being dependent on the rate of electrolysis, which is in turn controlled by an electric current. A further class of devices uses the same gas-driven principle, but generates this gas by chemical rather than electrical means. For example, U.S. Pat. No. 5,814,020, hereby incorporated by reference, describes a gas-powered infusion device where the gas is generated either by an electrolytic cell or by the reaction between citric acid and sodium bicarbonate; said reaction generating carbon dioxide and water.

The central problem with these gas-driven devices is that they all employ a gas-filled chamber in order to drive the drug infusion. As gases are very susceptible to changes in ambient temperature and air pressure, the danger of employing this principle is that a significant and undesirable change in the flow-rate will occur as such temperature or pressure changes occur. For example, a loss of pressure in an airplane could result in a sudden bolus being delivered at an inappropriate time. Similarly, a drop in temperature could result in the drug infusion stopping. For these reasons, despite massive development efforts, these products have faced considerable commercial obstacles to implementation. The prior art confirms the problematic nature of this issue: In a partial attempt to address this issue, U.S. Pat. No. 6,186,982 describes a flow-regulation chamber appropriate to the above-described devices which attempts to compensate for such temperature and/or pressure changes. Nonetheless, this issue of heat and pressure sensitivity is an inherent disadvantage inhibiting the commercialization of these products.

The prior art further describes a number of options for attachment of needles to such ambulatory infusion devices. In addition to the standard method of having the infusion device connected via a tube to the hollow needle, U.S. Pat. No. 5,527,288 describes the attachment of a rigid needle to the underside of the diffusion device such that adhesion of the device to the skin causes the needle to penetrate the skin; and U.S. Pat. No. 5,599,438 describes a similar device but with the addition that the needle is auto-injected into the skin after device attachment.

BRIEF SUMMARY OF THE INVENTION

It is an object of this invention to produce a drug delivery system wherein said system overcomes the heat and pressure sensitivities of the prior art gas-driven systems, thereby providing a stable and constant infusion device.

A further object of this invention is to provide an infusion device wherein the driving force does not directly determine the infusion rate, so that friction effects are negligible and manufacturing tolerances are less critical.

Another object of this invention is to produce a simple and disposable means of infusion in which the infusion rate for the drugs can be controlled by an electric current.

Yet another object is to provide a compact infusion unit which is microprocessor-controlled, said control relating to inputs including any combination of the following: an electronic timer, chemical or biomedical sensors, manual settings, and pressure sensors.

An additional object of this invention is to construct a simple, disposable propulsion means which is capable of delivering drugs in a timed pattern that can be attached or adopted to already existing infusion vehicles.

A further additional object of this invention is to create a simple and disposable infusion unit which can be employed in portable programmable infusion systems.

A still further additional object of this invention is to provide a bolus mechanism, whereby the patient can momentarily increase the infusion rate of the drug so as to deliver a bolus of the drug, without compromising the ongoing functioning of the infusion device.

A still further additional object of this invention is to provide a delivery system for drugs which is activated by a biomedical control system that reacts to stimuli related to bodily functions, such as temperature, pH, muscle contractions, chemical sensors inserted into the skin or body, electroencephalography, or electrocardiography and/or combinations of the above.

A still further additional object of this invention is to enable simple alterations of the drug infusion rate simply by changing the relative diameters of the drug and control chambers.

These and other objects may be obtained by means of a simple infusion system which is comprised of a pressure-generation means such as a spring, coupled to both a drug reservoir chamber and a control chamber, where the coupling is such that the control chamber serves to constrain the motion of the pressure-generation means, thereby limiting the displacement applied to the drug chamber.

More specifically, according to the present invention there is now provided a drug delivery infusion device comprising an injection means in fluid connection with a drug reservoir chamber and pressure-generation means coupled to both said drug reservoir and to a liquid filled controlled chamber, wherein the coupling is such that said liquid filled control chamber serves to constrain the motion of the pressure-generation means, thereby controlling the drug infusion rate, wherein said liquid filled control chamber is associated with means for controlled depletion of the liquid therein whereby depletion of the volume of liquid in said control chamber enables said pressure-generation means to drive the drug in said reservoir chamber therefrom for infusion thereof.

In preferred embodiments of the present invention said liquid filled control chamber is associated with means for generating gas from said liquid and further comprises gas-permeable walls, such that a gas generated from said liquid is released from the control chamber via said gas-permeable walls directly following its generation.

Preferably, said drug to be delivered is in liquid form.

Advantageously, by using a spring which is designed to deliver a force much stronger than the potential friction forces, said friction forces effects are rendered negligible, thereby reducing manufacturing tolerances, reducing manufacturing costs, and making the device more reliable.

A preferred embodiment of the control chamber comprises a gas-permeable section in at least part of the walls of said chamber and a gas-generation means, such that the gas generated is released from said control chamber via said gas-permeable section directly following its generation. As the liquid in this chamber is gradually converted to a gas, the volume of liquid remaining in the chamber is slowly depleted. By this arrangement, the displacement effected into the drug reservoir chamber is proportional to the rate of depletion of the liquid in the control chamber. Advantageously, even though the driving mechanism is a gas-generation one, there is no gas chamber and thus this mechanism is insensitive to ambient heat and pressure fluctuations.

The coupling between the pressure-generation means and the chambers may be achieved via a number of methods, including but not limited to: (a) various mechanical means for physically attaching them in order to move them together, either in parallel or in series, (b) the use of any kind of bar mechanism that can deliver proportional or other relative motion, (c) hydraulic, pneumatic, or magnetic coupling, (d) the use of slidable pistons connecting the chambers, (e) the use of levers and/or cogs, or (f) the subdivision of a chamber into a pressure-generation compartment and a drug delivery reservoir by a fluid tight septum, where said septum may be in the form of a flexible diaphragm or a slidable piston.

The drug reservoir chamber is in communication with means to convey the liquid drug to an injection site in the body of the recipient, such that pressure on this chamber causes the drug to be injected at said site. The injection site may either be an integral part of the infusion device or may be connected by a tube.

The gas-generation means may include electrolysis, a chemical reaction or evaporation; the key factor being that part of the liquid present in the control chamber is converted to a gas or a vapor. As this gas or vapor is produced, it emerges from the liquid chamber via the said gas-permeable wall section(s), which are at least partially constructed from a gas-permeable membrane. The result of said gas generation is thereby a gradual reduction in the remaining liquid volume in the control chamber.

Where the gas-generation means is electrolysis, the current required to electrolyze the liquid (i.e. the electrolysis solution) may be supplied by a power source such as a battery. The power source may be regulated by or attached to a control unit that is activated by an electronic timer, biomedical control unit controlled by a microprocessor or any other such means. For example, a biomedical control unit may be used which reacts to changes in bodily functions such as, temperature, pH, muscle contractions, electroencephalography, or electrocardiography, and/or any of the above in combination, to energize the electrodes by producing an electric current that varies in intensity according to the strength of the stimuli. Said biomedical control unit may be attached to the external ends of the electrodes by socket means or any other suitable electrical connection.

For many drugs, there is a requirement not only to deliver a steady ongoing infusion, but also to enable the delivery of a bolus at a specific time. For example, a patient will sometimes want to inject a bolus of insulin directly after meals. The present invention enables bolus delivery to be performed according to a number of methods, without detracting from the overall principle detailed above. These methods include: (a) mechanically repositioning the control chamber relative to the drug chamber; and (b) greatly increasing the electrolysis rate (where the gas is produced by electrolysis). In a preferred embodiment, a mechanism for mechanically repositioning the control chamber relative to the drug chamber is provided, either by unscrewing one end of the control chamber, changing the length of one of the piston rods, or just shifting the position of one of the chambers.

Lastly, the infusion device of the present invention preferably includes a means of blockage detection. Said detection means is important as, if a blockage develops, it is important (a) to inform the patient and (b) to ensure that there is no sudden unwanted bolus injected if and when such blockage clears. Preferably this blockage detection will be implemented by means of either a pressure detector integral to the injection means and/or an over-pressure valve which releases the excess liquid. Where a pressure detector is used together with an electrolysis-based gas generation means, the electrolysis can be halted until the blockage disappears. It should be noted that said over-pressure valve should be bypassed or blocked at bolus release.

By pre-loading the infusion device of the present invention with the desired drug, a method for the controlled delivery of a drug to a patient is provided.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE SEVERAL VIEWS OF THE DRAWINGS

FIG. 3 shows an isometric section view of the disposable device as per FIG. 2a; and FIG. 4 illustrates the construction of a semi-disposable version of the infusion device of the present invention, where FIG. 4c shows the permanent portion of the device, and FIG. 4d provides an isometric view of the assembly of FIG. 4b, emphasizing the spring housing guide and travel limit features.

DETAILED DESCRIPTION OF THE INVENTION

Figure 1:
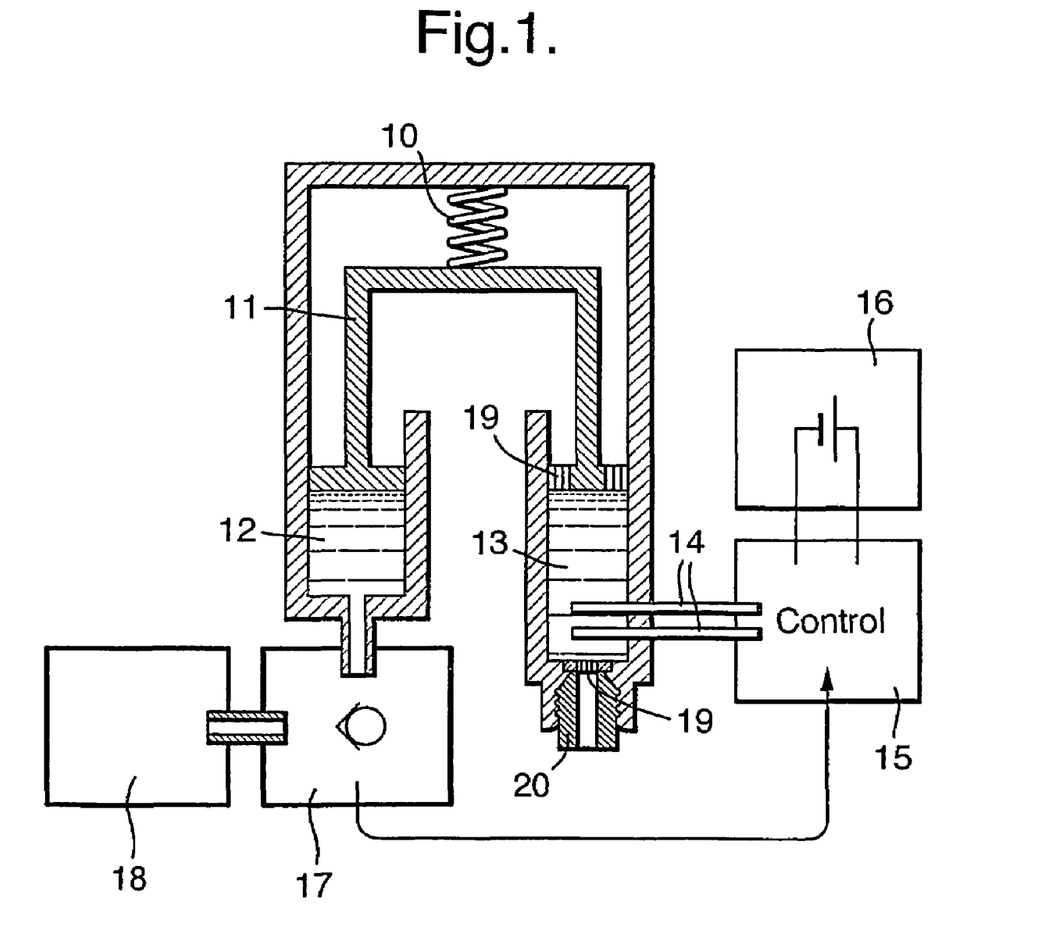
FIG. 1 shows a schematic representation of an embodiment of the infusion device of the present invention where the drug chamber and the control chamber are mounted in parallel.

FIG. 1 shows a schematic representation of the main functional elements of a disposable infusion device. Said device can be either attached to a strap or belt, or adhered to the body. In a preferred embodiment, the pressure-generation means driving the infusion is provided by a spring 10 such as a stainless steel "coil spring". Said spring serves to provide a source of force along the axis 11. Advantageously, the tolerance of this spring is not a critical factor in the design of the infusion device; it is sufficient that the force is provided in excess, albeit limited such that the pressure applied to the drug remains below the values that could be harmful to the body and/or are limited by regulations and standards. Said axis 11 in turn applies force to the contents of two chambers: the drug reservoir chamber 12 and the control chamber 13. In a preferred embodiment, the control chamber 13 contains an electrolysis solution (composed of water and salt) together with electrodes 14 for the electrolysis of said solution as known in the art and referred to above. Said electrodes 14 are powered by an integral battery 16, preferably via an electronic control circuit 15. As the walls of said chamber 13 contain a gas-permeable component 19, the gas thus generated by electrolysis within the chamber 13 exits the chamber 13. As the electrolysis proceeds, the water is gradually converted into hydrogen and oxygen, and thus the remaining volume of water is gradually reduced, enabling the axis 11 to advances the pistons into both chambers (12 and 13) in parallel. The drug chamber 12 is in fluid connection with an injection means 18 via an over-pressure detection means 17. The injection means 18 may be a hollow needle integral to the device of the present invention, a connector to a tube which in turn connects to an external hollow needle, or a connection to a nozzle suitable for a specific application such as artificial insemination, nasal drug delivery, etc. For specific uses and drug requirements, this nozzle or outlet can be a connector (such as a Luer Lock connector) to either a specific infusion set or to a standard set. Additionally, said outlet can be sealed by means of a cap or a welded foil. Furthermore, said outlet can incorporate a valve or a stop-cock for enabling tube or infusion set interchanging. Said valve can comprise a septum on said drug outlet together with a needle on the tube set terminal, having the needle penetrate the septum as the connector is engaged, thereby making a drug connection to the set. In a preferred embodiment the injection means 18 is a delivery set in which a drug is infused through a catheter that penetrates the dermis. In this case, a needle is then used only as a support for the insertion process and removed immediately afterwards. In a further preferred embodiment, said injection means 18 is a hollow needle which is initially enclosed within the device and then inserted into the dermis mechanically once the device has been attached to the patient's skin. In a still further preferred embodiment, said hollow needle is rigidly attached to the exterior of the housing such that application of the device to the skin causes the needle to penetrate the dermis. As will be clear to those skilled in the art, a dedicated insertion device may be used for the insertion of the infusion needle or catheter whether it is inserted at a remote infusion site or is integral to the device. The over-pressure detection means 17 serves to prevent the build-up of liquid pressure along the liquid path to the injection means 18 in order to detect a blockage. In the case of such blockage detection, it is important that further pressure not develop, as the sudden release of a blockage could cause an undesirable bolus to be injected. Thus the primary task and main safety factor of such a means is to drain the excess drug via a pressure valve so as to prevent this occurring. Note that said over-pressure valve is a safety feature not only in the case of drug path blockage but also in case of any breakage in the control chamber 13. Such a breakage may result in transferring the entire spring force to the drug chamber 12. A further fail-safe mechanism to deal with this problem is to have two parallel control chambers, so that if one breaks the other continues to function. In a preferred embodiment, said overpressure detection means 17 is connected to the electronic control circuit 15 in order to achieve two desirable objectives: (a) to signal said circuit 15 to issue an audible or visible alarm to announce that a blockage has been detected, and (b) to reduce the current flow to the electrodes 14 so as to curtail the electrolysis and thus implement a reverse feedback loop. For applications requiring long term use and/or intensive electrolysis rates, special care has to be taken of the electrodes 14 to prevent deterioration or sediments. Such special care means known in the art include periodic switching of the polarity of the electrodes.

Figure 2A:
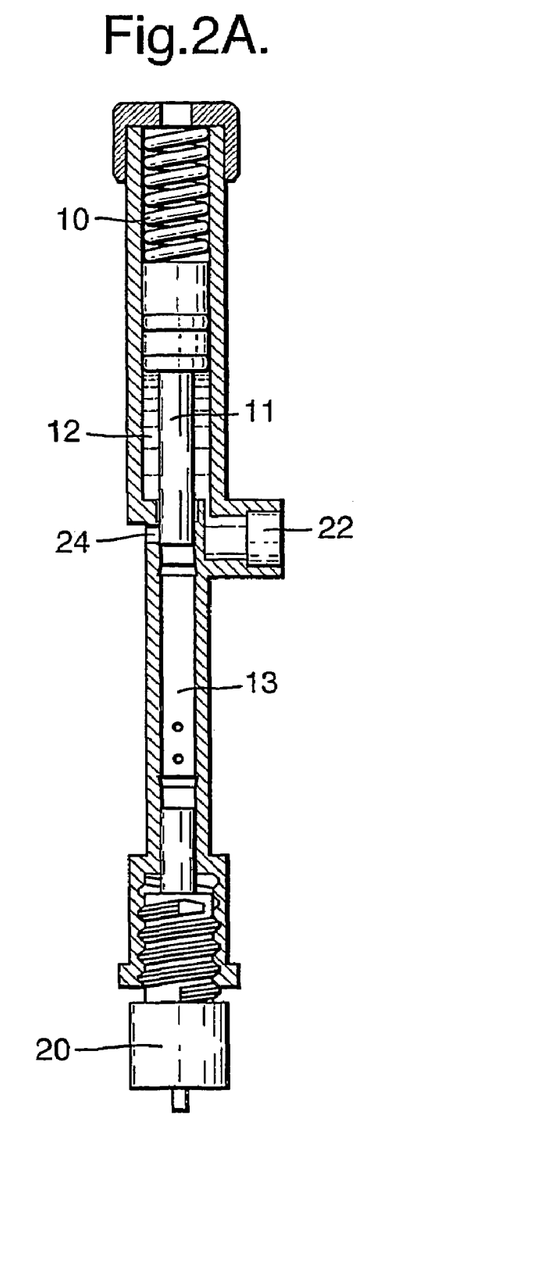
FIG. 2 provides two cross-sectional views of a disposable infusion device where the drug chamber and the control chamber are mounted in series.

Referring now to FIG. 2a, a sectional view of a preferred embodiment of a disposable infusion device is shown. In said embodiment, the drug chamber 12 and the control chamber 13 are coupled in series as opposed to the parallel coupling shown in FIG. 1 above. As in the configuration of FIG. 1, the spring 10 is shown applying pressure to the liquid in the control chamber 13 which, in turn, limits the displacement of the piston 11 into the drug chamber 12 and thus ensures that the drug delivery rate is proportional to the rate at which liquid is expelled from the control chamber 13. In a preferred embodiment, the shapes of both cells resemble cylinders or syringes into which the piston 11 with a sealing means can be inserted. Said sealing means may employ a rubber seal or other tightly-lubricated fit so as to frictionally yet snugly engage the inner walls of the chambers, such that a liquid seal is formed and maintained as the piston 11 advances. Said sealing means is generally applicable to any pistons employed in various configurations of the device, including the parallel embodiment shown in FIG. 1. As before, the decrease in volume of the liquid in the control cell 13 determines the rate of displacement of said axis and thus this displacement defines the drug delivery rate. A septum valve 22 is provided to enable filling of the drug into the infusion device. Said filling may be performed either by the provider of the device or by a doctor or patient close to the time of use. In this embodiment, a well ventilated section is maintained between the drug cell 12 and the liquid cell 13 so as to avoid any lick from one cell to another. In the case of any accidental lick from one of said cells, said lick will be exhausted via the vent hole 24. In order to enable a patient-controlled bolus to be delivered by the infusion device, the piston 11 must be allowed to advance into the chambers in a relatively rapid manner. Said bolus delivery mechanism is also important for priming; i.e. for filling the delivery set or injection means with drug prior to connecting to the body. To these ends, in a preferred embodiment of this bolus-delivery means, the far end of the control chamber 13 is not held by a fixed support but is instead held by a bolus release piston 20, which can be threaded out through a fixed wall in the housing, preferably by using a knob accessible to the patient. The screw-turn action thus implemented can be geared with a linear travel knob, or with several knobs each turning the bolus release piston 20 at different rates for different bolus sizes. Note that in this embodiment, the threading mechanism is designed such that said bolus release piston 20 can only be turned in one direction, and that each revolution or part of a revolution is accompanied by an audible click. The purpose of this click is to enable the user to clearly control the size of the bolus delivered. As bolus deliveries are typically in the range 0.001 ml to 1.0 ml, in a preferred embodiment each click will correspond to 0.01 to 0.1 ml, or more preferably will fall in the range of 0.03 ml to 0.07 ml. If, for example, it is determined that each click corresponds to 0.05 ml, then 2 clicks will deliver a small bolus of 0.1 ml, and 10 clicks will deliver a large bolus of 0.5 ml. A further preferred embodiment of the bolus delivery means, which is applicable only to the case where the electrolysis is employed to convert the liquid into gas, is to increase the rate of electrolysis significantly, under control of the electronic control circuit 15.

Figure 2B:
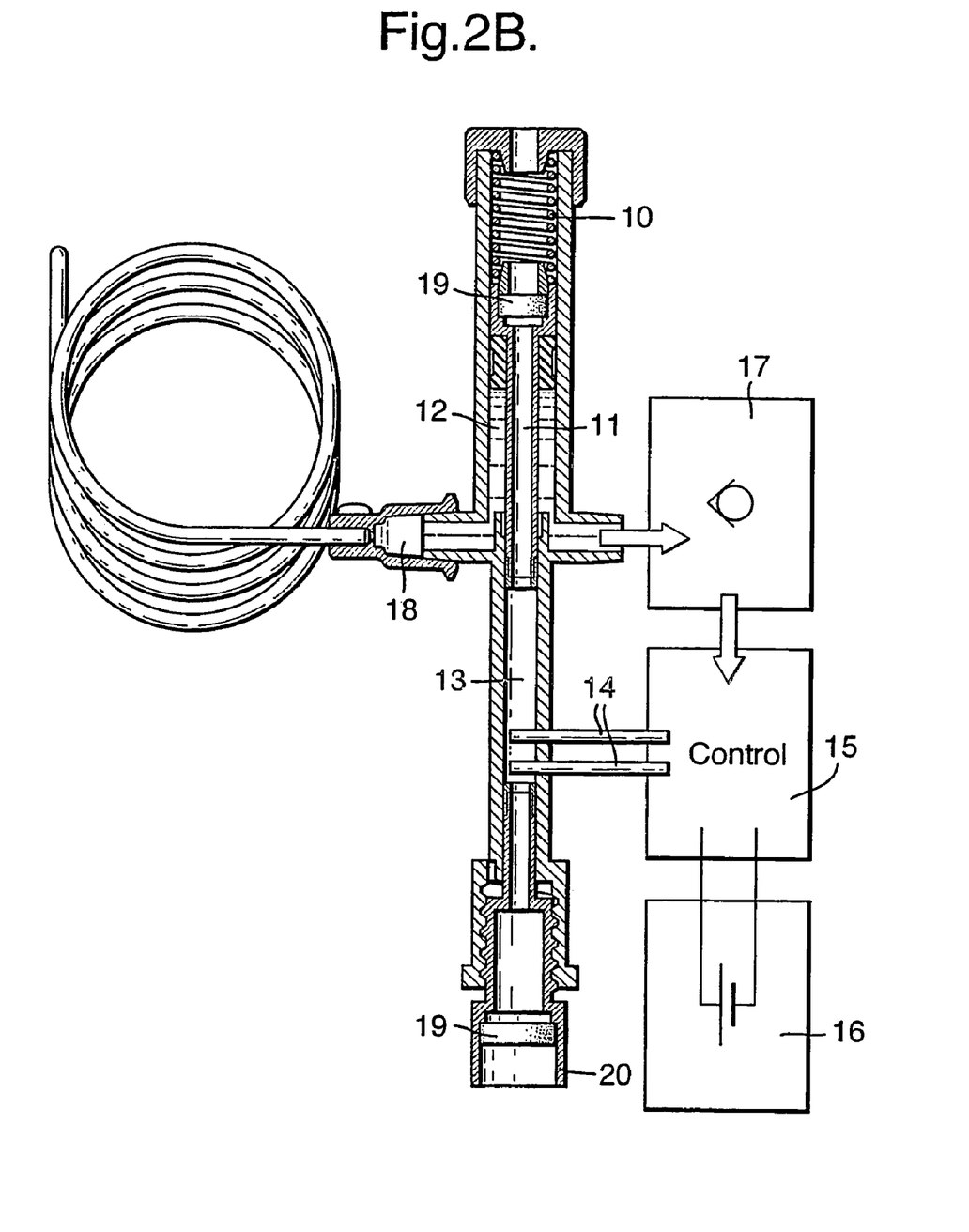

Referring now to FIG. 2b, a cross-sectional view illustrating the operation of the mechanism of FIG. 2a within the context of the complete device is shown. In particular, the liquid connection between the drug chamber 12, the injection means 18 and the over-pressure detection means 17 (connected in parallel) is shown. In a preferred embodiment, said injection means 18 is connected via a Luer Lock connector on the drug cell outlet. Said connector carries a cap or a sealed welded foil which is removed before use and replaced by the tubing and injection site set. As before, the over-pressure detection means 17 is connected to the electronic control unit 15 so as to reduce the electrolysis rate at the electrodes 14 when a blockage is detected.

Figure 3:
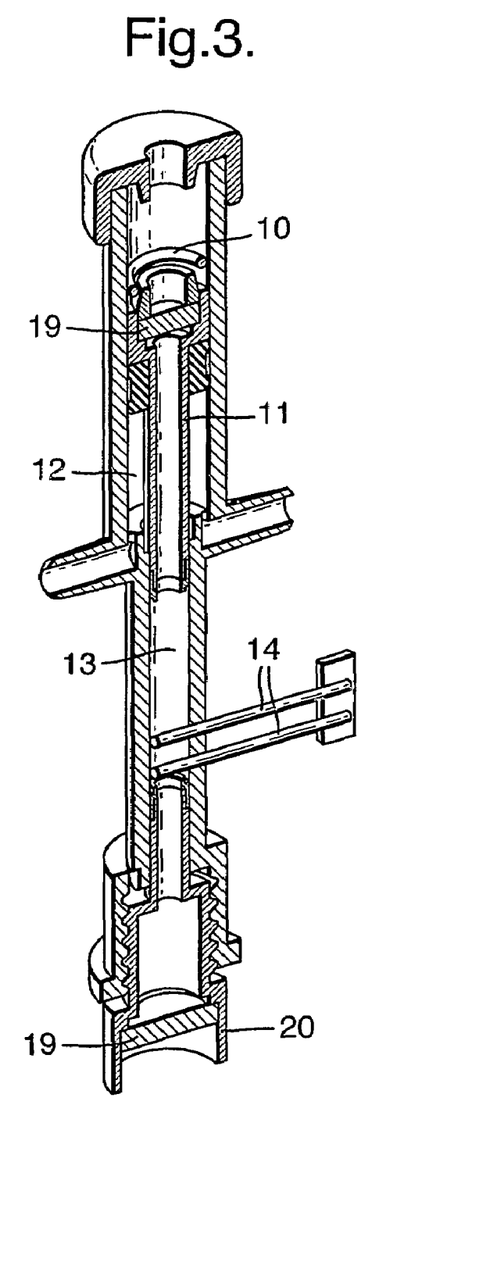
Figure 4A:
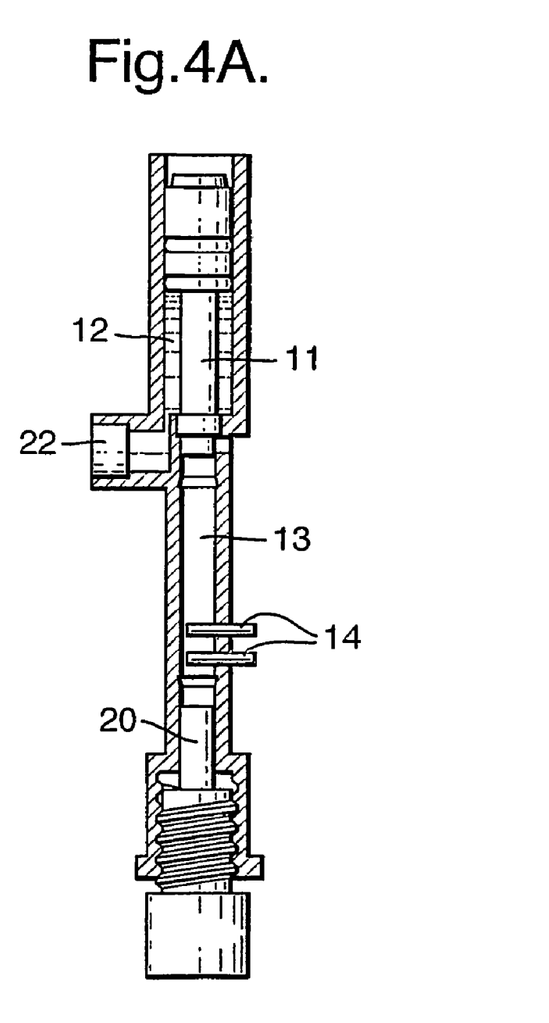
FIG. 4a shows the disposable cartridge.
Figure 4B:
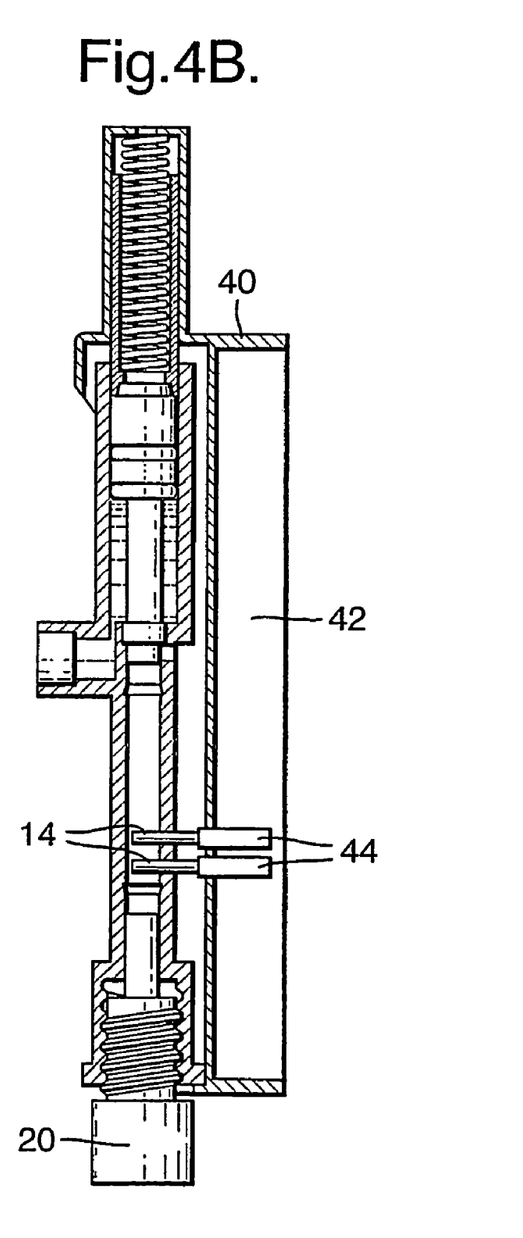
FIG. 4b shows the assembly of said disposable cartridge in the permanent device.
Figure 4C:
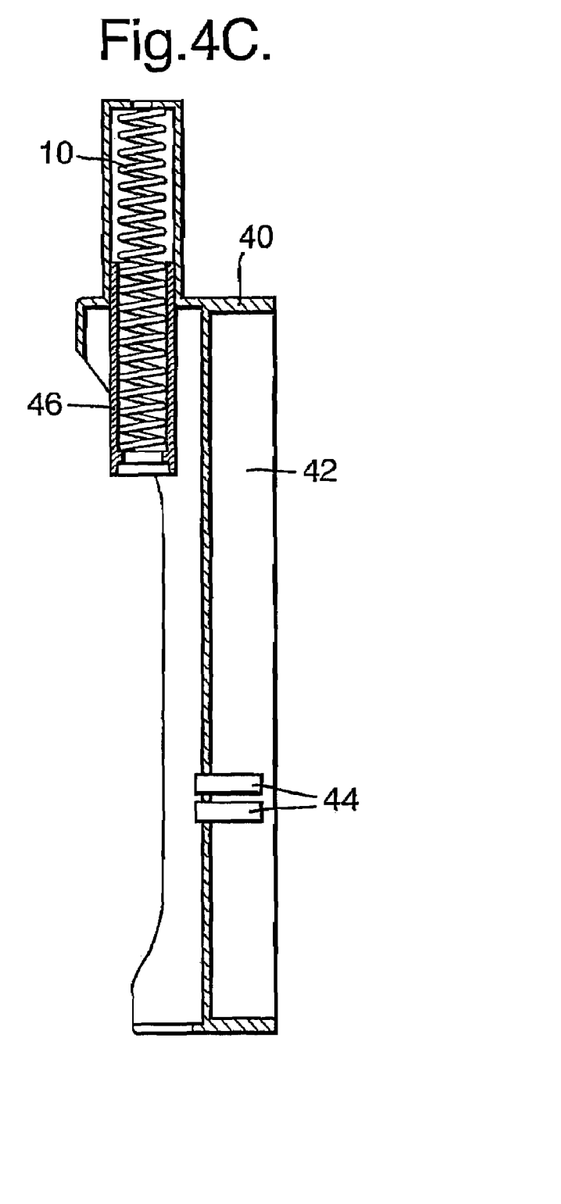
Figure 4D:
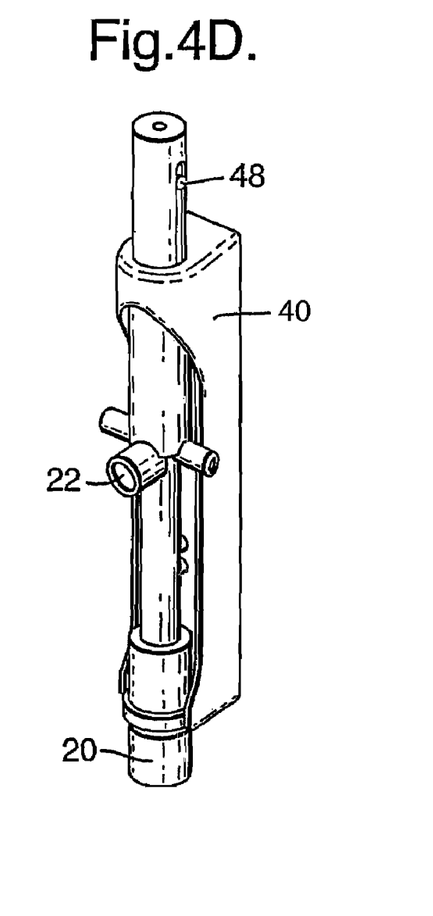

Referring now to FIG. 3, an isometric view of the assembly described in FIG. 2a above is shown, illustrating the hollow nature of both the piston 11 and the bolus release piston 20. This construction ensures that an unbroken liquid connection is maintained between the liquid in the control cell 13 and the gas-permeable membrane 19 sections or stoppers. Said membrane 19 is typically provided with a backing support such as a grill (not shown) in order to provide structural support. In a further preferred embodiment said membrane 19 is located in just one of the pistons, or inset into the walls of the control chamber 13. A key element of the device of the present invention is that, as gas or vapor is generated inside the control cell 13, said gas or vapor is vented by said membrane 19. To this end, a liquid impermeable but gas permeable material is used for the membrane 19; for example FLUOROPORE™ membrane from Millipore Inc. (Billerica, Mass.) or EMFLON™ membrane from Pall Inc. (East Hills, N.Y.).

FLUOROPORE™ is a hydrophobic polytetrafluoroethylene (PTFE) which is often used in venting applications, has very good chemical compatibility, and is completely impermeable to water.

Infusion devices such as the device of the present invention need to be able to introduce anywhere between 1 ml and 20 ml, over a time range of a few hours to a few days. Typically a disposable device such as this will deliver a few ml over 24, 48 or 72 hours, and will need to support a continuous, settable, infusion rate of 0.001 ml/hr to 0.350 ml/hr. In a preferred embodiment, the method used to convert the liquid in the control chamber 13 into gas (or vapor) will be electrolysis, the liquid will be water, and the infusion rate will be settable via the electronic control circuit to anywhere in said 000.1 ml/hr to 0.350 ml/hr rate. In a preferred embodiment of the electronic control circuit 15, said rate will either be settable in explicit numbers, for example inputting a number between 1-350 (inclusive) using a button or buttons, or similarly inputting a code which corresponds to a given rate. Such codes can include any combination of letters or numbers, or words such as "slow", "medium," "fast", etc. Additional preferred methods for converting the liquid in the control chamber into gas (or vapor) include: (a) evaporating the liquid using direct heat, vibration (such as ultrasonic vibration) or passing an electric current through the water; and (b) the use of a chemical reaction such as the combination of citric acid with sodium bicarbonate as per some prior art devices, where a gas is one of the reaction products.

To illustrate the functioning of the control chamber 13, an example of the gas generation required to provide a steady drug infusion rate of 0.1 ml/hr is described herein. The volume of liquid which needs to be removed from the control chamber 13 in order to deliver a given drug volume is a function of the effective areas of the pistons acting within the two chambers. Thus, in the embodiment depicted in FIG. 2, where the effective areas of the pistons have a 1:4 ratio, then only 0.025 ml of liquid need be removed from the control chamber 13 in order to deliver 0.1 ml of drug. However, in the embodiment depicted in FIG. 1, where the piston areas are identical, 0.1 ml of liquid must be removed from the control chamber 13 in order to achieve the same result; as described below. On electrolysis, a mole of water (18 ml) is transformed into one mole of hydrogen gas (H) and one half mole of oxygen gas ($O_2$), or approximately 33 L in volume. In mole terms, 0.1 ml of water is equivalent to 0.0056 moles, which occupies 33×0.0056 L=0.18 L. Thus, gas venting of 0.18 L/hr is required via the membrane 19. Note that air flow rates for Fluoropore™ membrane range from below 0.15 L/min/cm$^2$ to 20 L/min/cm$^2$ (based on a differential pressure of 10 psi), which is more than an order of magnitude greater than that required by the device of the present invention. Accordingly, only a small plug of this material is required to provide sufficient venting for the gas generation rates envisaged in the infusion device of the current invention.

In a preferred embodiment, the electric control circuit 15 serves to control the overall functioning of the device, including on/off control, setting of the continuous delivery rate, alerting the patient to blockage detection conditions, limiting the flow rate during a blockage, providing a bolus, totaling time and volume parameters of usage and interfacing with various body function sensors as are known in the art. In a preferred embodiment, the infusion device of the present invention will respond (using said circuit) to physiological or chemical changes detected during use, so as to provide a self-monitoring, feedback functionality. Such "closed loop" systems include the use of the infusion device of the present invention as an insulin pump controlled by the electronic control circuit 15 connected to a glucose sensor. The rate or frequency of insulin administration is controlled by the microprocessor according to the instantaneous blood glucose level measured by the sensor. Because a system of feedback similar to natural homeostatic regulation is used, such a closed loop insulin delivery system may also be referred to as an "artificial pancreas". Monitored stimuli for actuating microprocessor control of the drug delivery may also be those related to bodily functions, such as temperature, pH, muscle contractions, electroencephalography, or electrocardiography, and/or a combination of the above.

Of course numerous other drugs besides insulin can be delivered to the patient using the infusion device of the present invention. Typical medicaments suitable for use with the device according to the invention include peptides, proteins or hormones such as insulin, calcitonin, calcitonin gene regulating protein, atrial natriuretic protein colony stimulating factor, betaseron, erythropoietin (EPO), interferons such as a, b or g interferon, somatropin, somatotropin, somatostatin, insulin-like growth factor (somatomedins), luteinizing hormone release hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methodone, lidocaine, bupivacaine, diclofenac, naproxen, paverin, and analogues thereof; anti-migraine agents such as sumatriptan, ergot alkaloid, and analogues thereof; anti-coagulant agents such as heparin, hirudin, and analogues thereof; anti-emetic agents such as scopolamine, ondanesetron, domperidone, metoclopramide, and analogues thereof; cardiovascular agents, anti-hypertensive agents, and vasodilators such as diltiazem, clonidine, nifedipine, verapamil, isosorbide-5-mononitrate, organic nitrates, agents used in the treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; antidiuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof. Additional candidates for infusion from the present device include a solution containing sperm for artificial insemination and nasally ingested medications.

Referring now to FIG. 4, a semi-disposable embodiment of the infusion device of the present invention is shown. In this embodiment, FIG. 4a shows a disposable cartridge containing the drug 12 and control chambers 13. Said cartridge may be inserted into the permanent housing 40 shown in FIG. 4c. As said cartridge is inserted, the spring 10 is compressed into the spring guide 46 as shown in the assembled view shown in FIG. 4b. Said spring guide 46 then retracts into the housing 40, with its travel being limited via the engagement of the prolongations 48 of the spring guide 46 with the guiding slots in the housing 40 as shown in FIG. 4d. Assembly of the disposable cartridge into the permanent device in this manner also causes the various connectors between the said cartridge and the said permanent device to interlock. Thus, the electrical contacts 44 attach to the electrolysis electrodes 14, and the electronics module 42 connects to various inputs and/or output signals including the over-pressure detections means, temperature or others sensors, wireless telemetry means, etc.

Advantageously, by employing a permanent device with a disposable cartridge, sophisticated (and more expensive) electronics can be employed as it is not a recurring expense. Additional features that can be introduced into the electronics module 42 include: the use of a rechargeable battery, the transmission of parameters for wireless storage or display, and the interfacing to various sensors which monitor the patient's physical, chemical or biological parameters. A further motivation for employing this semi-disposable configuration is to overcome sterilization obstacles. As certain sterilization methods can damage specific components of the system or be inefficient, separating the device into components enables different sterilization routines to be used for different components. For instance, Gamma radiation is an effective sterilization means for the drug and liquid chambers but may cause harm to some electronic components. Accordingly, separating the device into its components and packing them separately overcomes that problem. A later packaging procedure may then merge them into one package. Similarly, the electronics module 42 and/or the spring 10 may also be designed to be reused a limited number of times. The site and tubing set can also be packed and sterilized separately as well, as the patient may want to use the same site/tubing set for a longer period then the drug set due, and therefore wish to interchange two or three drug cartridges while not having to dismount the site from the body.

Note that in the figures provided, the specific structure shown is exemplary and modifications in shape and size may be readily made by one skilled in the art to provide functional equivalents. The chambers are shown as cylindrical but may be any other suitable shape. Similarly, the drug chamber and the control chamber may not be as shown but rather of different relative diameters, in order to achieve a different relationship between the rate of contraction of the control chamber and the rate of drug infusion. Further, the means for controlled depletion of the liquid in the control chamber not only includes the previously described gas generation means of electrolysis, a chemical reaction and evaporation, but also includes additional methods of gradually expelling a liquid from the control chamber exist, that do not require the use of a gas-permeable membrane. Such methods include: a diffusion mechanism from the control chamber to the atmosphere, evaporation through a hydrophilic wall, evaporation through a wick that connects the control chamber and the atmosphere, osmotic migration, and the use of a liquid outlet through a flow-limiting vent. When using the above evaporation methods, said evaporation can be executed in controlled conditions where the temperature and humidity are controlled, in order to further increase accuracy. Additionally, said means for gradual liquid expulsion can be located in a further chamber connected to the control chamber via a pipe or a hole. One advantage of such an embodiment is that a valve can be added in between the two chambers, which will shut down when it detects that the outlet is clogged, thereby constituting a useful safety feature. A further advantage is that this configuration enables the conditions causing the liquid expulsion to be removed from the main liquid reservoir, and this is especially advantageous in the case of water heating.

It will be evident to those skilled in the art that the invention is not limited to the details of the foregoing illustrative embodiments and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A drug delivery infusion device comprising an injection means in fluid connection with a drug reservoir chamber and pressure-generation means coupled to both said drug reservoir and to a liquid-filled control chamber containing a drug, wherein the coupling is such that said liquid-filled control chamber for providing a drug infusion at a controlled and steady rate serves to constrain the motion of the pressure-generation means, thereby controlling a drug infusion rate, wherein said liquid-filled control chamber is associated with means for controlled depletion of the liquid therein whereby depletion of the liquid in said control chamber enables said pressure-generation means to drive a drug in said reservoir chamber therefrom for infusion thereof.

2. A drug delivery infusion device according to claim 1 wherein said liquid-filled control chamber is associated with means for generating gas from said liquid and further comprises gas-permeable walls, such that a gas generated from said liquid is released from the control chamber via said gas-permeable walls directly following its generation.

3. The infusion device of claim 1 wherein said drug is in liquid form.

4. The infusion device of claim 3 wherein the drug reservoir chamber is in liquid communication with means to convey the liquid drug to an injection site in the body of the recipient, such that pressure in said drug reservoir chamber causes the drug to be injected at said site.

5. The infusion device of claim 1 wherein the coupling between the pressure-generation means and said drug reservoir chamber and said liquid-filled control chamber is such that the amount of drug driven from the drug reservoir chamber is proportional to the rate of depletion of the liquid in the control chamber.

6. The infusion device of claim 5 wherein said coupling between the pressure-generation means and said chambers is implemented by slidable pistons, which are pushed by said pressure-generation means into said chambers.

7. The infusion device of claim 5 wherein said coupling between the pressure-generation means and said chambers is implemented by a flexible diaphragm constituting a movable wall within said chambers.

8. The infusion device of claim 1 where the drug reservoir chamber and the control chamber are coupled in parallel, wherein said coupling is connected to the pressure-generation means.

9. The infusion device of claim 1 wherein the drug reservoir chamber and the control chamber are coupled in series with said pressure-generation means.

10. The infusion device of claim 1 wherein an infusion set is an integral part of the infusion device.

11. The infusion device of claim 1 wherein an infusion set is connected to the infusion device by a tube.

12. The infusion device of claim 1 wherein the volume of liquid in the control chamber is gradually reduced by the at least partial conversion of said liquid into a gaseous phase by a gas-generation means; wherein said gaseous product exits said chamber.

13. The infusion device of claim 12 wherein said gaseous products exit from said control chamber via a gas-permeable membrane.

14. The infusion device of claim 12 wherein said gas-generation means include electrolysis, a chemical reaction, and evaporation.

15. The infusion device of claim 14 wherein the rate of said electrolysis is controlled by means selected from the group consisting of an electronic timer, a microprocessor, and a biomedical control unit.

16. The infusion device of claim 15 wherein said means is a biomedical control unit which reacts to bodily functions selected from a group consisting of a glucose sensor, other chemical or biological sensors, body temperature, pH of body fluids, muscle contractions, electroencephalography, electrocardiography, and combinations thereof.

17. The infusion device of claim 1 wherein the volume of liquid in the control chamber is gradually reduced by venting said liquid from the liquid chamber by a controlled method selected from the group consisting of osmotic migration, diffusion, controlled evaporation through a wick or hydrophilic wall, and mechanical flow interference utilizing a means selected form the group consisting of a labyrinth or an orifice.

18. The infusion device of claim 1 wherein said device further comprises an over-pressure detection means for determining the presence of a blockage in the injection means.

19. The infusion device of claim 18 wherein said over-pressure detection means further comprises a valve for release of said pressure.

20. The infusion device of claim 1 settable, to deliver between 0.001 ml/hr to 0.35 ml/hr on a continuous basis.

21. The infusion device of claim 1 further comprising a bolus-delivery means.

22. The infusion device of claim 21 wherein said bolus-delivery means can deliver a bolus between 0.001 ml and 11.0 ml.

23. The infusion device of claim 1 wherein the drug in the drug chamber is selected from the group consisting of peptides, proteins, hormones, analgesics, anti-migraine agents, anti-coagulant narcotic antagonists, chelating agents, antianginal agents, chemotherapy agents, sedatives, anti-neoplastics, protaglandins and antidiuretic agents.

24. The infusion device of claim 1 wherein said device is a disposable device.

25. The infusion device of claim 1 wherein said device comprises a permanent portion and a disposable portion.

26. The infusion device of claim 1 wherein said device is comprised of separate components including a drug cartridge, a control unit and a tube set.

* * * * *